United States Patent
Squilla et al.

(10) Patent No.: US 7,245,753 B2
(45) Date of Patent: Jul. 17, 2007

(54) METHOD FOR DETERMINING DENTAL ALIGNMENT USING RADIOGRAPHS

(75) Inventors: John R. Squilla, Rochester, NY (US); John T. Boland, Fairport, NY (US); John P. Spoonhower, Webster, NY (US)

(73) Assignee: Carestream Health, Inc., Rochester, NY (US)

(*) Notice: Subject to any disclaimer, the term of this patent is extended or adjusted under 35 U.S.C. 154(b) by 761 days.

(21) Appl. No.: 10/606,709

(22) Filed: Jun. 26, 2003

(65) Prior Publication Data

US 2006/0120582 A1 Jun. 8, 2006

(51) Int. Cl.
*G06K 9/00* (2006.01)

(52) U.S. Cl. ........................... 382/128; 382/154

(58) Field of Classification Search ............. 382/128, 382/132, 154; 345/420; 433/233
See application file for complete search history.

(56) References Cited

U.S. PATENT DOCUMENTS

| | | | | |
|---|---|---|---|---|
| 3,949,478 A * | 4/1976 | Schinhammer | ............... | 433/3 |
| 4,837,732 A * | 6/1989 | Brandestini et al. | .......... | 433/29 |
| 5,273,429 A * | 12/1993 | Rekow et al. | ............... | 433/215 |
| 5,372,502 A * | 12/1994 | Massen et al. | ............... | 433/215 |
| 5,452,219 A * | 9/1995 | Dehoff et al. | ............... | 700/163 |
| 5,851,115 A * | 12/1998 | Carlsson et al. | ............ | 433/215 |
| 5,857,853 A * | 1/1999 | van Nifterick et al. | ..... | 433/213 |
| 6,068,482 A | 5/2000 | Snow | ............... | 433/223 |
| 6,163,620 A | 12/2000 | Hojnacki et al. | ........... | 382/162 |
| 6,195,474 B1 * | 2/2001 | Snyder et al. | ............... | 382/312 |
| 6,512,994 B1 * | 1/2003 | Sachdeva | ................... | 702/167 |
| 6,648,640 B2 * | 11/2003 | Rubbert et al. | ................ | 433/24 |
| 2005/0084144 A1 * | 4/2005 | Feldman | ...................... | 382/128 |
| 2005/0177266 A1 * | 8/2005 | Kopelman et al. | .......... | 700/117 |

FOREIGN PATENT DOCUMENTS

| | | |
|---|---|---|
| EP | 1 276 072 A1 | 1/2003 |
| WO | 01/80763 A2 | 11/2001 |
| WO | WO 01/80763 A2 * | 11/2001 |

OTHER PUBLICATIONS

U.S. Appl. No. 09/796,239, filed Feb. 28, 2003, John P. Spoonhower et al.
U.S. Appl. No. 09/894,627, filed Jun. 28, 2001, John T. Boland et al.
The Image Processing Handbook by John C. Russ. 2nd ed., CRC Press, 1995, pp. 201-208.
"The CEREC System by Sirona", Academy of Computerized Dentistry of North America. http://www.acd-us.com/Cerec%20Sirona.htm.

* cited by examiner

*Primary Examiner*—Joseph Mancuso
*Assistant Examiner*—Nancy Bitar (57) ABSTRACT

A method for determining dental alignment of a 3-dimensional model of one or more teeth of a patient comprises the steps of: (a) obtaining a radiograph of the teeth of the patient; (b) obtaining a digital image from the radiograph indicative of the dental alignment of the teeth relative to a dental arch of the patient; (c) overlaying the 3-dimensional model of the teeth with the digital image obtained from the radiograph; (d) determining vertical and horizontal misalignment of the teeth in the 3-dimensional model relative to the digital image obtained from the radiograph; and (e) adjusting the 3-dimensional model to correct for the misalignment, thereby producing an adjusted 3-dimensional model of the teeth that is corrected for the vertical and horizontal alignment of the teeth relative to the dental arch.

11 Claims, 13 Drawing Sheets

METHOD FOR DETERMINING DENTAL ALIGNMENT USING RADIOGRAPHS

FIELD OF THE INVENTION

The invention relates generally to the field of dental radiography, and in particular to the use of a dental radiograph to generate a model for a dental prosthesis.

BACKGROUND OF THE INVENTION

The creation of a dental prosthesis requires very precise fit and alignment to the prepared tooth, as well as to the adjacent and opposing teeth. In this discussion, a prosthesis may be a crown for a single tooth or a bridge to replace a number of teeth. In general, the dentist is concerned with achieving the proper fit for: the prosthesis and the prepared tooth, the spacing between the adjacent teeth, the biting surfaces of the opposing teeth, and the vertical and horizontal alignment of the teeth as part of the dental arch.

The dominant method currently used to achieve the required alignment is a dental impression, which provides a geometrically precise, 3-dimensional model of the area. While successful, this method requires multiple office visits in order to be used. These visits prolong the process, increase cost, and take up chair time that could be used for other patients. Some concepts have been developed, primarily for use on an individual tooth, wherein only a single office visit is necessary. For example, in Sirona's CEREC system (Sirona Dental Systems GMBH, Bensheim, Germany), an optical scanning procedure is used to replace the conventional impression. In this system, an optical impression is imaged using structured light, and computer-based methods are used to determine the size and shape of the desired prosthesis. Computer-based methods are also used to create the prosthesis.

There are other methods that do not make use of a dental impression. Instead of a physical impression, these methods use direct images or scans of the patient's teeth. For example, U.S. Pat. No. 5,604,817, entitled "Tooth Measurement without Calibration Bodies" and issued to Massen et al. on 18 Feb. 1997, describes a method for the optical three dimensional measurement of a tooth without the use of calibration bodies arranged around the tooth. An optical projection system projects a pattern onto a tooth, and an optical imaging system images the pattern projected thereon, from a first position in space and subsequently from a second position in space, with the images from the two positions in space having a common imaged area of the tooth. The image patterns are evaluated to calculate three dimensional coordinate data of the tooth surface relative to the respective imaging position for each image and also for the two images combined, to produce a single three dimensional tooth surface data record. U.S. Pat. No. 5,372,502, entitled "Optical Probe and Method for the Three-Dimensional Surveying of Teeth" and issued to Massen et al on 13 Dec. 1994, describes an optical oral or mouth probe which is utilized for the three-dimensional measurement or surveying of teeth. The probe projects a particular pattern onto the teeth, which is distorted by the teeth. The measuring probe captures the distorted pattern and transmits it to a computer, which recreates the topography of the teeth.

In commonly-assigned, copending U.S. patent application Ser. No. 09/894,627, entitled "Method and System for Creating Dental Models from Imagery" and filed in the names of J. T. Boland, J. P. Spoonhower and J. R. Squilla, a dental model is created from a series of images of an intra-oral object, where the object includes common surface features and a control target arranged with respect to the object to provide control features. The common features, and the control features from the control target imaged with the images of the object, are measured for a series of images. Then a 3-dimensional model of the object is analytically generated by photogrammetrically aligning the measurements of the control features. The model is then adjusted by aligning the common features of the model to like features on the image of the intra-oral object, thereby producing an aligned dental model from the series of images.

In U.S. Pat. No. 6,068,482, entitled "Method for Creation and Utilization of Individualized 3-Dimensional Teeth Models" and issued to Michael Desmond Snow on 30 May 2000, a standard 3D model of a standard patient's teeth is individualized for a specific patient. A combination of the standard 3D model and either a scanned 2D x-ray image or a scanned 2D image of a plaster cast impression taken of the patient's teeth is projected by a computer system, where the x-ray image or the plaster cast image is projected as a background for the standard 3D model. The standard 3D model is then rotated, translated and scaled by the user so as to match the orientation of the background image. The resultant optimized 3D individualized model is then saved and used as a patient record for treatment planning and record keeping. In one described usage in an orthodontics practice to demonstrate the effect of braces, the differences between the standard model and the individualized model are mapped, and the computer system "animates" the differences to illustrate the movement of the teeth during treatment from the individualized model to the idealized standard model.

In using the direct imaging method of the prior art on multiple teeth, especially if dental impressions are not used, then the precise curvature data (of the teeth as part of the dental arch) is needed from another source. The present invention makes use of dental radiographs to geometrically describe the vertical alignment of a patient's teeth, which provides the needed information. By projecting the x-ray, a fitted curve, or the outline of the teeth onto a computer representation of the prosthesis (prior to fabrication), the vertical alignment of the arch (as indicated by the size, position and orientation of the teeth) can be confirmed and/or adjusted.

SUMMARY OF THE INVENTION

The present invention is directed to overcoming one or more of the problems set forth above. Briefly summarized, according to one aspect of the present invention, a method for determining dental alignment of a 3-dimensional model of one or more teeth of a patient comprises the steps of: (a) obtaining a radiograph of the teeth of the patient; (b) obtaining a digital image from the radiograph indicative of the dental alignment of the teeth relative to a dental arch of the patient; (c) overlaying the 3-dimensional model of the teeth with the digital image obtained from the radiograph; (d) determining vertical and horizontal mis-alignment of the teeth in the 3-dimensional model relative to the digital image obtained from the radiograph; and (e) adjusting the 3-dimensional model to correct for the mis-alignment, thereby producing an adjusted 3-dimensional model of the teeth that is corrected for the vertical and horizontal alignment of the teeth relative to the dental arch.

A method is described wherein dental radiographs are used to geometrically describe the vertical alignment of a patient's teeth. Dental radiographs and measurement techniques, including software, are used to map the relative vertical position of a patient's teeth as compared to the adjacent teeth. This data is used to ensure proper shape, size, and placement of dental prostheses prior to fabrication.

The invention has the distinct advantage of not having to rely on dental impressions, while speeding up the process, reducing material cost, and increasing patient comfort. Moreover, a prosthesis can be properly fitted without multiple office visits.

These and other aspects, objects, features and advantages of the present invention will be more clearly understood and appreciated from a review of the following detailed description of the preferred embodiments and appended claims, and by reference to the accompanying drawings.

DETAILED DESCRIPTION OF THE INVENTION

Because dental image processing methods are well known, the present description will be directed in particular to elements forming part of, or cooperating more directly with, a method in accordance with the present invention. Elements not specifically shown or described herein may be selected from those known in the art. Certain aspects of the embodiment to be described may be provided in software. Given the method as shown and described according to the invention in the following materials, software not specifically shown, described or suggested herein that is useful for implementation of the invention is conventional and within the ordinary skill in such arts.

Figure 13:
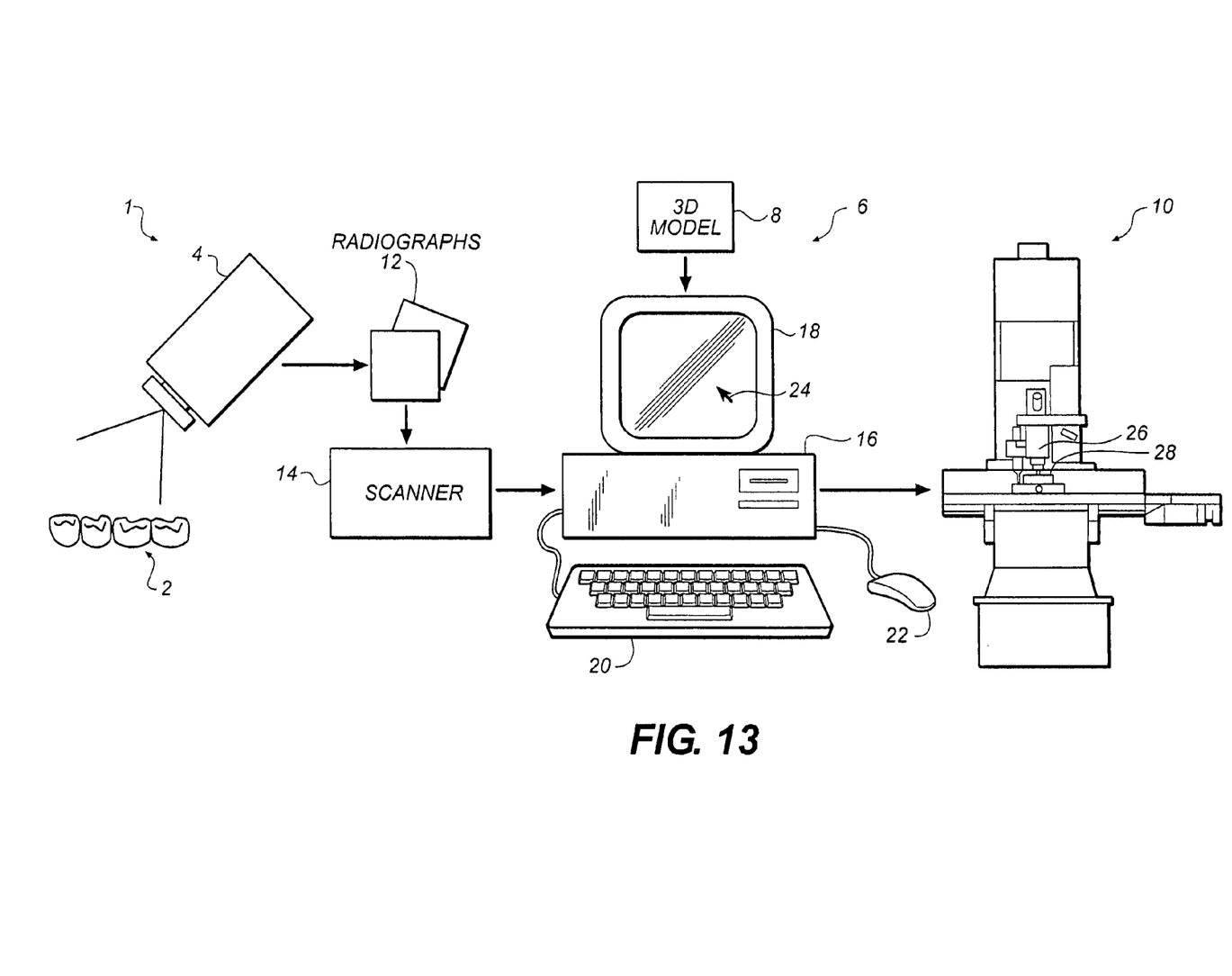
FIG. 13 is a diagram of a dental system that utilizes the method(s) shown in the preceding figures.

Referring initially to FIG. 13, a preferred embodiment of the invention is implemented in a system including a capture stage 1 for capturing images of one or more teeth 2 with a camera 4, a computer system 6 including instructions for implementing the invention in connection with a 3-dimensional model 8 of a prosthesis, and a machine tool 10. In the schematic shown in FIG. 13, it should be understood that the interconnections between the camera 4, the 3-dimensional computer model 8, the computer system 6 and the machine tool 10 are shown by arrows, and therefore not specifically indicated. These interconnections may take various forms, such as a cable, a network (such as a local area network or the Internet) or any other electromagnetic connection (such as an rf transmission), or the manual transfer of data from machine to machine. The camera 4 is a dental x-ray camera that produces dental radiographs 12 which geometrically describe the vertical and/or horizontal alignment of a patient's teeth, in particular the alignment of one or more teeth in relation to adjacent or opposing teeth. The radiographs 12 (after development) are scanned in a scanner 14 and the scanned radiograph data is provided to the computer system 6.

The 3-dimensional prosthetic model 8 may be provided from various sources, including from a scanned image of a physical impression of the teeth 2 or from one or more digital images of the teeth 2. In the latter case, the digital images may be provided from the capture stage 1, which for this purpose includes any type of conventional dental camera that is capable of capturing a reasonably high resolution digital image of the teeth 2; a preferred example is the intra-oral camera disclosed in commonly assigned, copending U.S. patent application Ser. No. 09/796,239, entitled "Intra-Oral Camera with Integral Display", filed Feb. 28, 2001 in the names of J. P. Spoonhower, J. R. Squilla and J. T. Boland, and which is incorporated herein by reference. The digital image(s) may then be used to generate the 3-dimensional model 8 of the prosthesis; a preferred method for creating such 3-dimensional models is described in the aforementioned commonly-assigned copending U.S. patent application Ser. No. 09/894,627, which is incorporated herein by reference.

The camera 4 is positioned by the dentist (or a dental assistant) and several images are ordinarily captured of the teeth 2; it is understood, however, that the orientation of the camera relative to the teeth may vary from one image to the next. The scanned radiographic data (from radiographs 12) from the camera 2 is transferred to the computer system 6 for processing. The methodology of the invention is implemented by the computer system 6 in its processor 16, and the imaging results may be interactively displayed on a monitor 18. An operator using a keyboard 20 and/or a mouse 22 can manipulate a cursor 24 to perform measurements and adjustments of the type that will be subsequently described. Alternatively, the measurement and/or adjustments may be performed automatically by software in the processor 16. The output from the computer system 6 is a digitized three-dimensional surface pattern, based on an adjusted 3-dimensional model 8, that is transferred to the machine tool 10 as a tool path program for the fabrication of a dental mold or a restorative piece. The program will direct a milling cutter 26 in the milling of the tooth mold or the restorative piece 28 from a suitable substrate, for example, ceramic or any other suitable machinable material that is useful for an intra-oral restoration.

Figure 1:
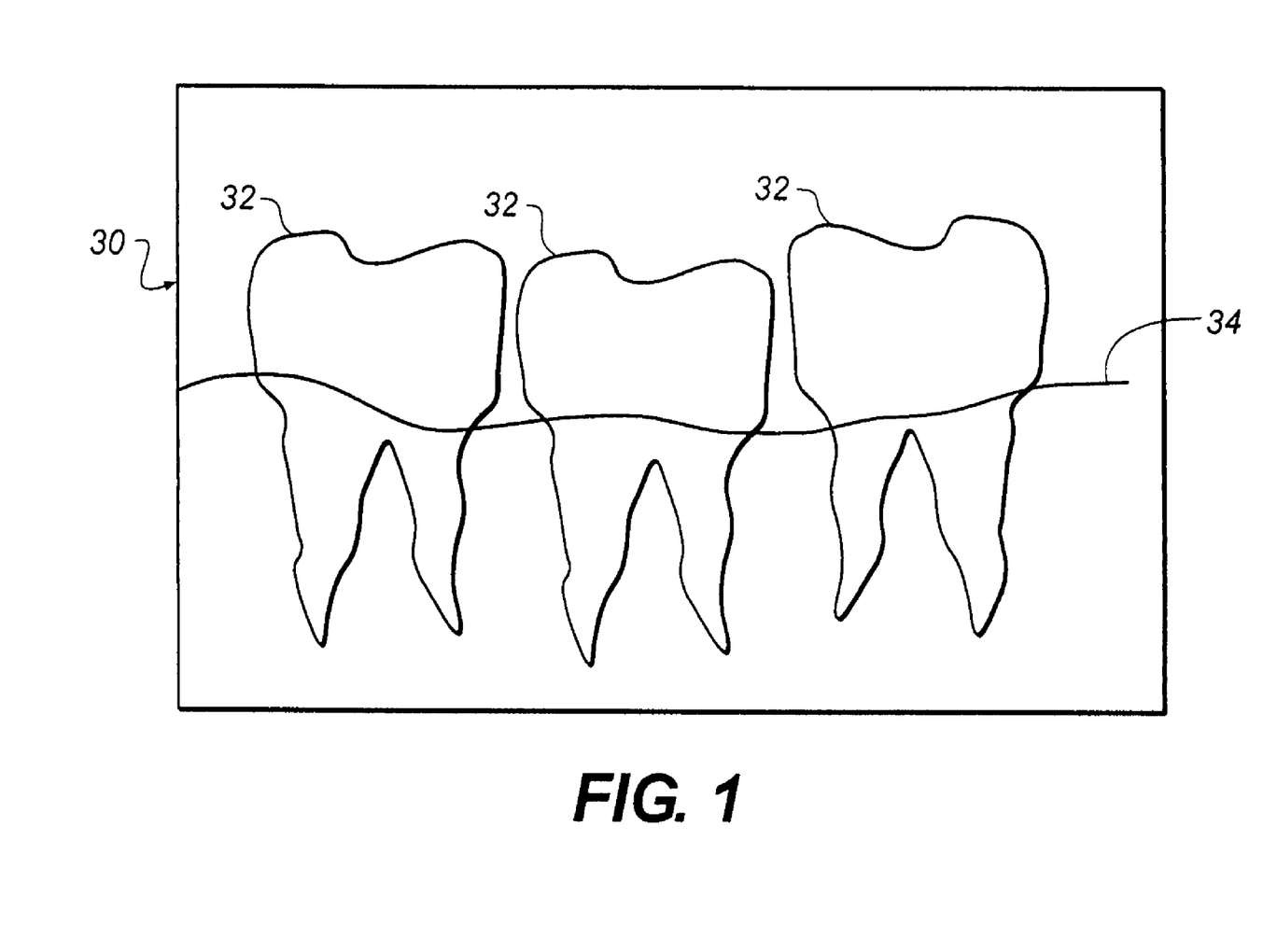
FIG. 1 shows a dental x-ray image in which imaged teeth exhibit a noticeable arch in a vertical direction.
Figure 2:
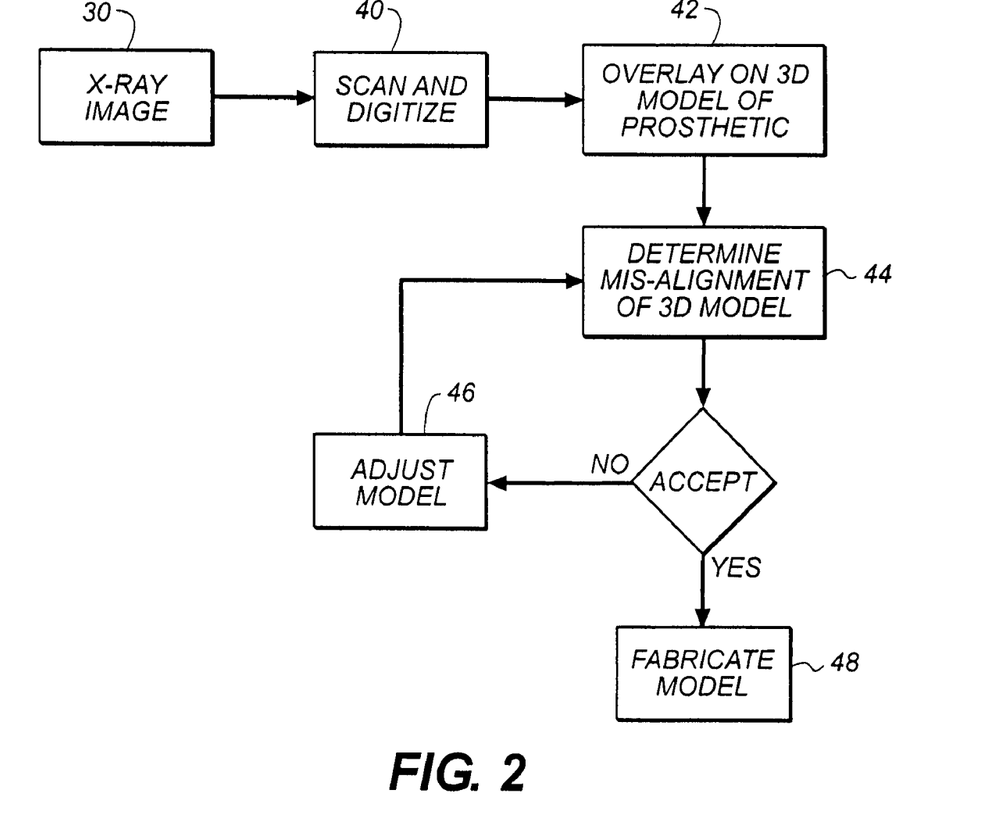
FIG. 2 shows a block diagram of a process in which the x-ray image shown in FIG. 1 is scanned and digitized, and then displayed in an overlay fashion on a 3D model of the prosthesis.

FIG. 1 shows an example dental x-ray image 30 in which the imaged teeth 32 exhibit noticeable arch in the vertical direction as can be seen in particular relative to a gum line 34. In FIG. 2, the x-ray image 30 is scanned and digitized in a scanning stage 40, where the image thus obtained is indicative of the dental alignment of the teeth relative to the dental arch. This image is then displayed in an overlay stage 42 in an overlay fashion on the 3D model 8 of the prosthesis. The misalignment between the overlay and the 3D model is determined in an alignment stage 44 and removed by adjusting the size, shape, and position of the teeth involved in the prosthesis in an adjustment stage 46. Once the overlay of the x-ray and the 3D model match sufficiently, the prosthesis can be fabricated in a fabrication stage 48.

If the process is done manually, the misalignment is visually observed in the alignment stage 44, optionally with computer-aided prompts, and the adjustment is performed in the adjustment stage 46 by using the cursor 24 (FIG. 13) and conventional software tools to drag, stretch, move or otherwise adjust the vertical and horizontal shape of the teeth in the 3-dimensional model 8 to conform, at least substantially, to the vertical and horizontal shape of the teeth in the x-ray image. For this purpose, the 3-dimensional image could be the active image, that is, subject to the software selection tools, and the x-ray image would be a passive background image. Accordingly, the curvature of the teeth in the 3-dimensional model (i.e., of the teeth as part of the dental arch) is matched to the curvature of the teeth in the dental x-ray image.

If the process is done automatically, either the user may select potential alignment points in the alignment stage 44 or such points may be automatically presented to the user through the graphical user interface of the monitor 18. After the alignment points are refined to the liking of the user, acceptance is signaled through manipulation of the mouse 22 or the keyboard 20. The result is a set of refined points that are suitable for the adjustment process in the adjustment stage 46. When thus done automatically, an exemplary process may generate a polynomial function to relate the alignment points. In its simplest form, the polynomial (alignment equation) is of the form $$X = a_1 + a_2 X' + a_3 Y'$$

with only three constants (and a similar equation for Y). Hence, locating three reference (alignment) points that are common to the two images allows one to be rotated and stretched (warped) to align with the other. (See pages 201-208 on Alignment in *The Image Processing Handbook, Second Edition*, by John C. Russ, CRC Press, 1995). Typically, more points are involved in the process. For instance, in commonly-assigned U.S. Pat. No. 6,163,620 (entitled "Automatic Process for Detecting Changes Between Two Images"), which is incorporated herein by reference, between five and one hundred tie points are used. The polynomial function is then used in the adjustment stage 46 to warp the 3-dimensional model to the x-ray image 30. Once alignment is completed, the results may be reviewed on the monitor 18. If the user deems the alignment adequate, acceptance is signaled through manipulation of the mouse 22 or the keyboard 20; otherwise, the process is returned to the alignment stage 44 and repeated in an iterative manner until the alignment results are acceptable to the user.

Figure 3:
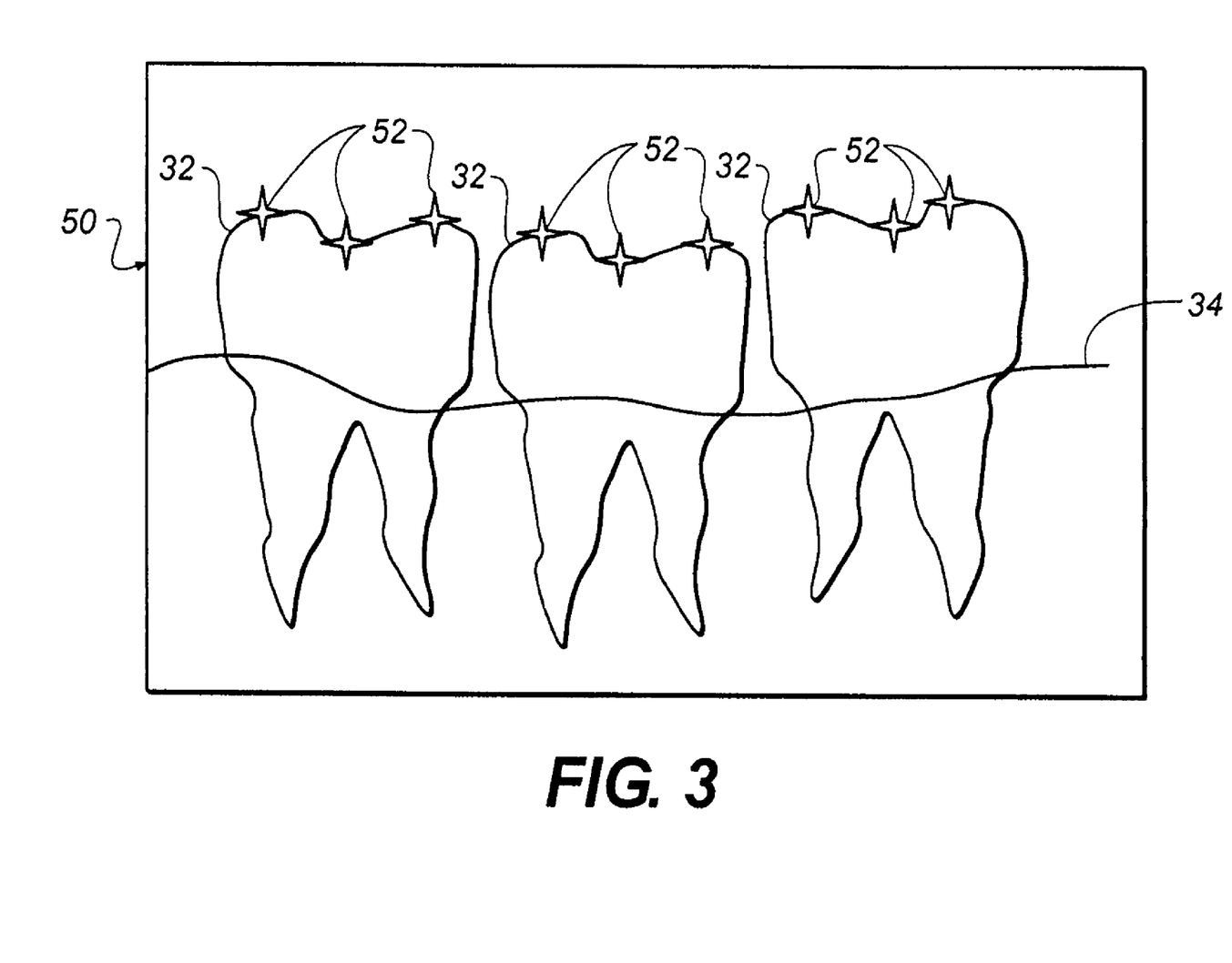
FIG. 3 shows an x-ray image with key vertices indicated.
Figure 4:
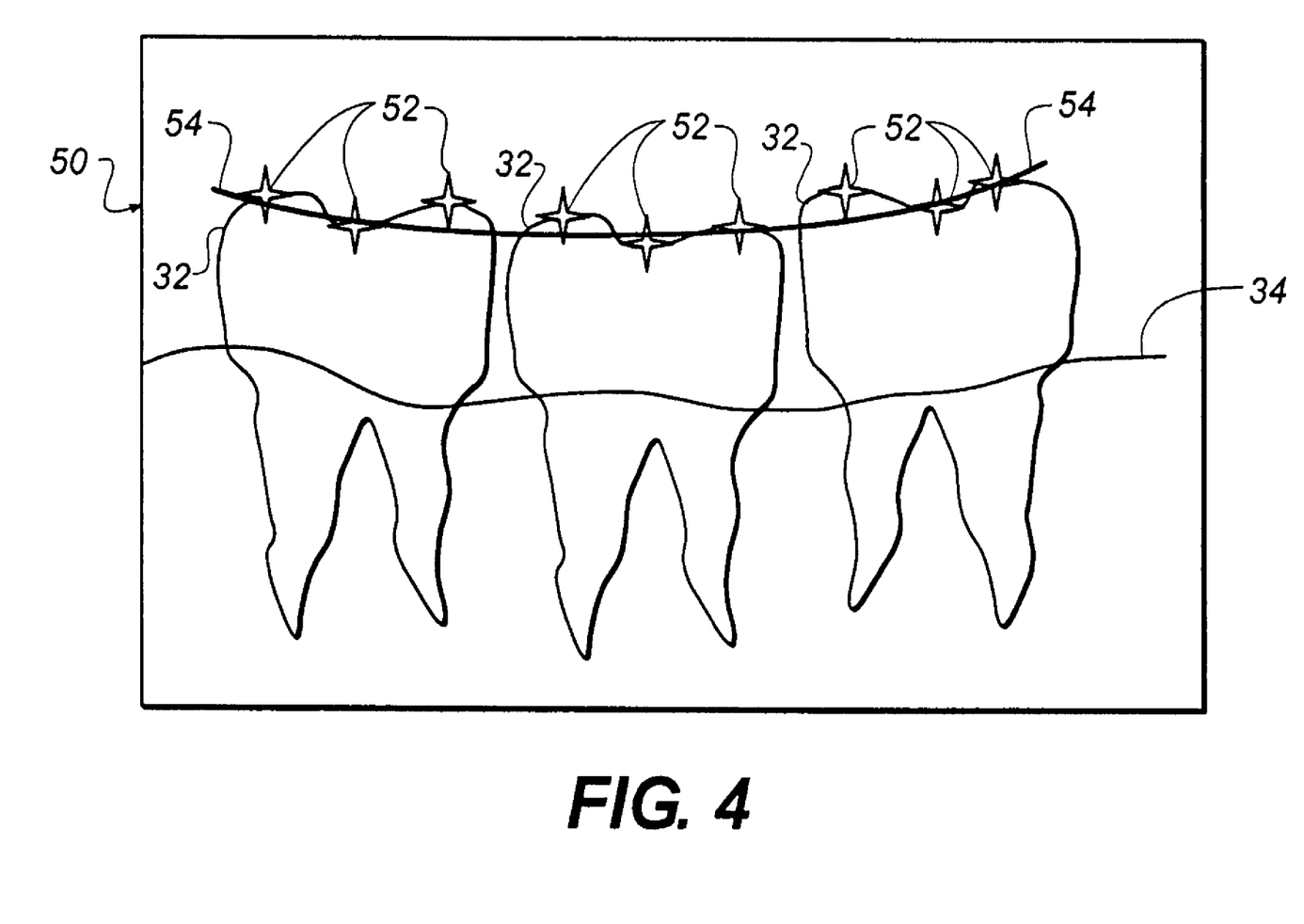
FIG. 4 shows an x-ray image with a fitted curve through the vertices indicated in FIG. 3.
Figure 5:
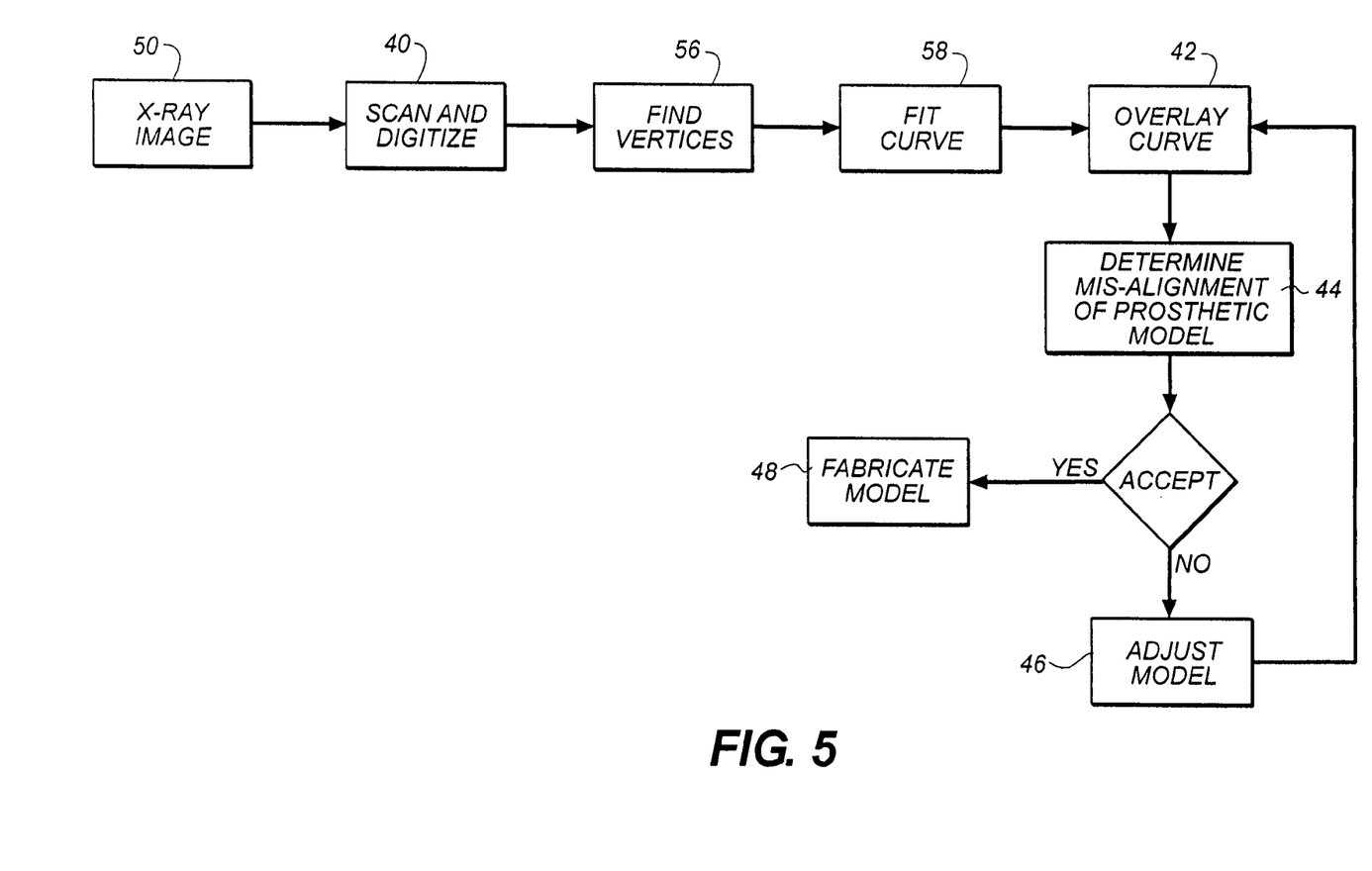
FIG. 5 shows a block diagram of a process for displaying the curve shown in FIG. 4 in an overlay fashion on the 3D model of the prosthesis.

FIG. 3 shows a similarly scanned and digitized x-ray image 50 with key vertices 52 indicated on the imaged teeth 32. FIG. 4 shows a curve 54 fitted through the vertices. In FIG. 5, where previously described stages have the same reference characters, the vertices 52 are found in a vertices search stage 56, in which the vertices may be located manually by means, e.g., of the cursor 24 (FIG. 13) or automatically by means of an edge sensitive algorithm, and a curve fitting stage 58 fits the curve 54 through the vertices 52 using, e.g., a least squares fit algorithm. In this embodiment, the image thus obtained of the curve 54 is indicative of the dental alignment of the teeth relative to the dental arch. The vertices curve 54 is then displayed in an overlay fashion in the stage 42 on the 3D model of the prosthesis. As described above in relation to FIG. 2, the misalignment between the overlay and the 3D model is determined in the alignment stage 44 and removed in the adjustment stage 46 by adjusting the size, shape, and position of the teeth involved in the prosthesis. Once the overlay of the curve and the 3D model match sufficiently, the prosthesis can be fabricated in the fabrication stage 48.

Figure 6:
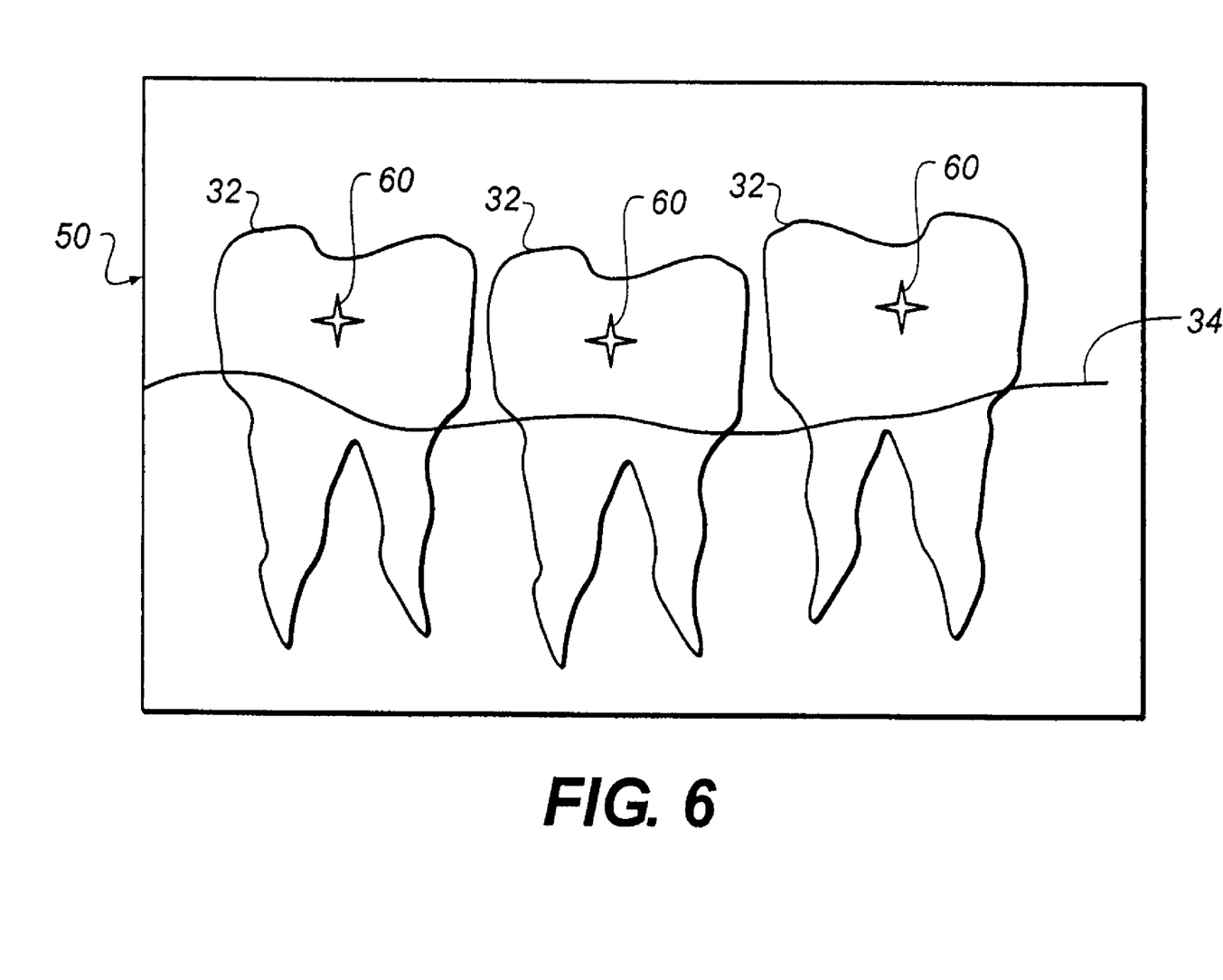
FIG. 6 shows an x-ray image illustrating an alternative method wherein the center of mass is computed for each tooth.
Figure 7:
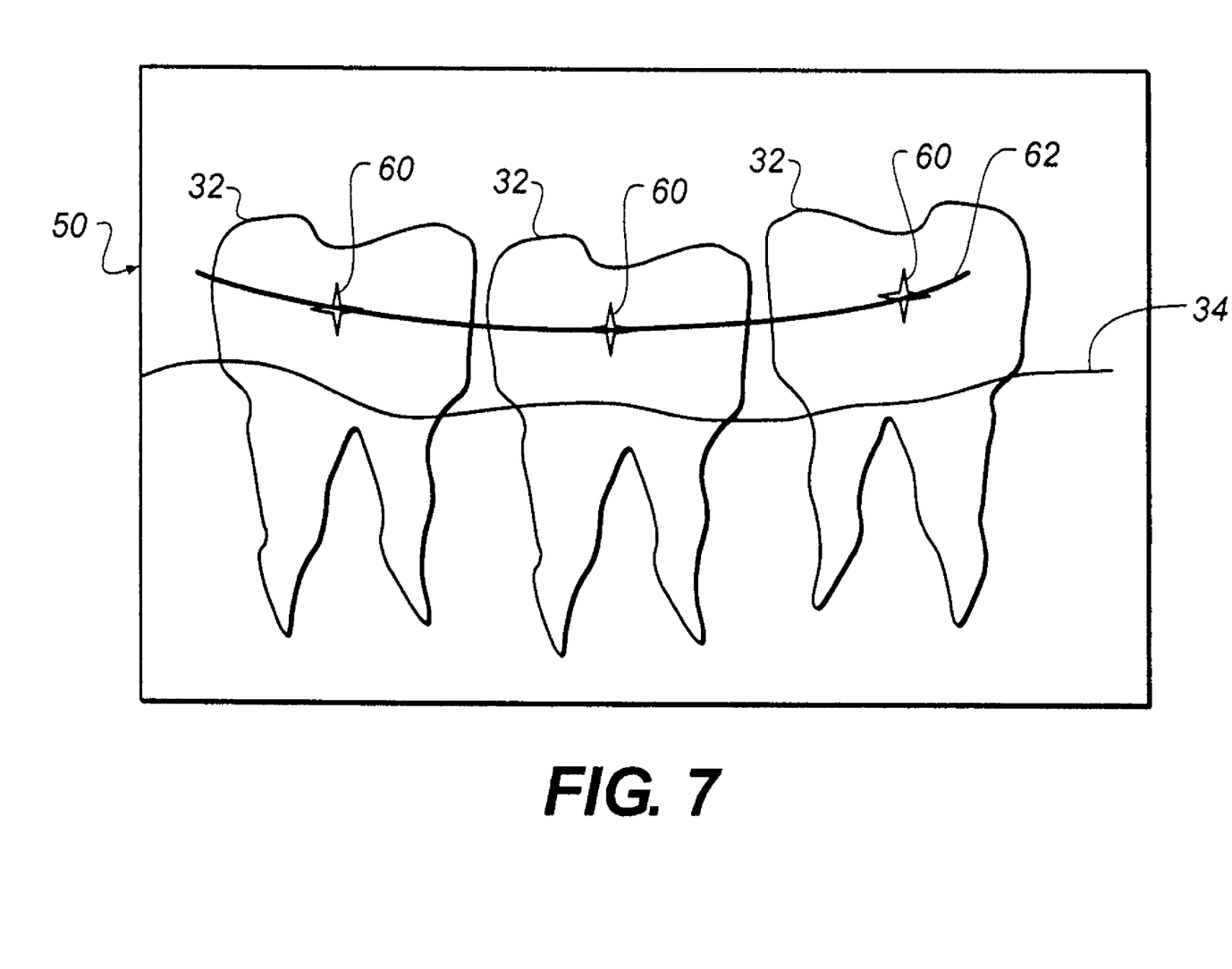
FIG. 7 shows an x-ray image with a curve fitted to the center of mass points shown in FIG. 6.
Figure 8:
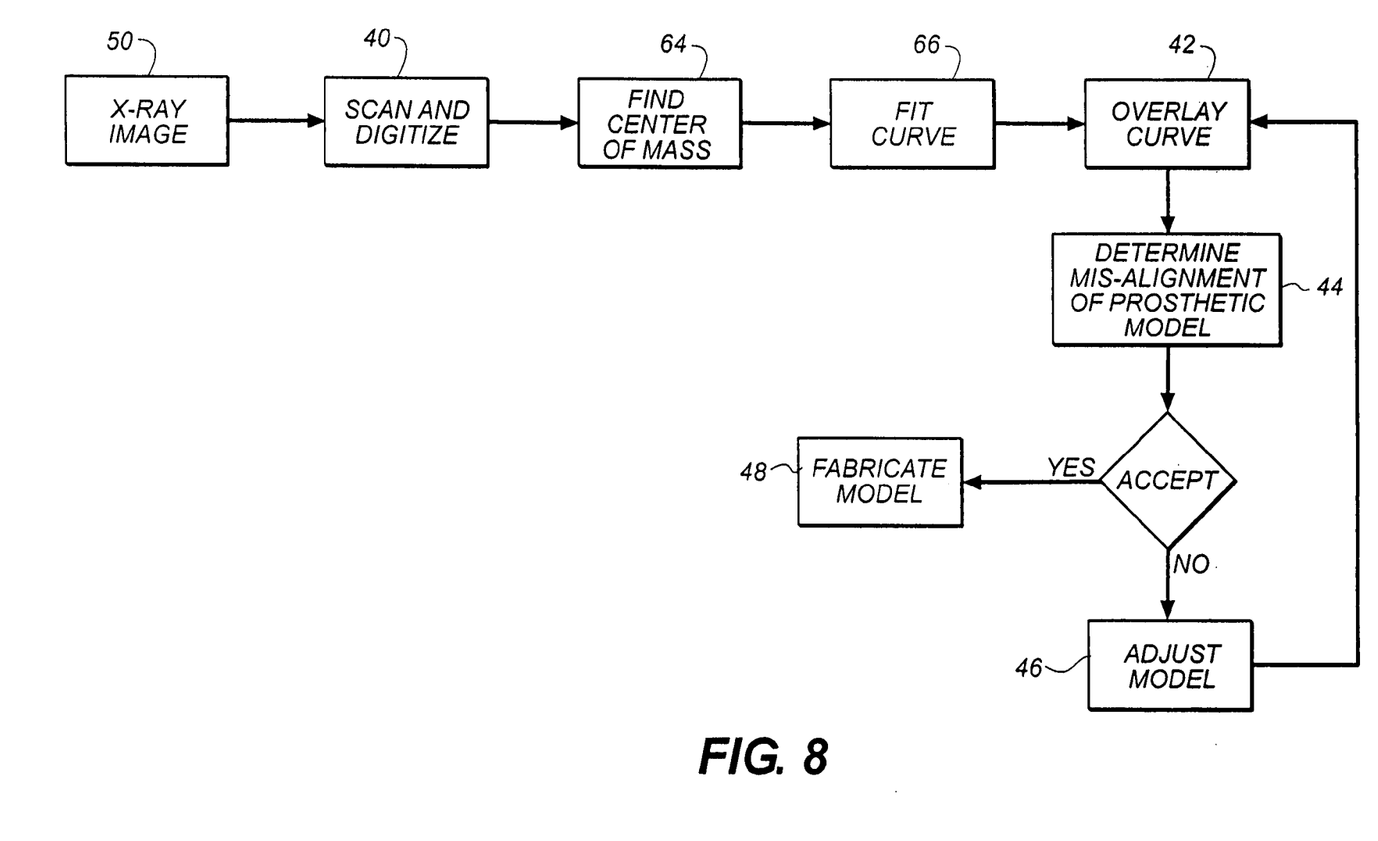
FIG. 8 shows a block diagram of a process for displaying the curve shown in FIG. 7 in an overlay fashion on the 3D model of the prosthesis.

FIG. 6 shows an example x-ray image 50 of an alternative method wherein a center of mass 60 is computed for each imaged tooth 32 and a curve 62, as shown in FIG. 7, is fitted to those points 60. In FIG. 8, a comparison/adjustment process similar to FIGS. 2 and 5 is followed, where the centers of mass are located in a center of mass stage 64 and the curve 62 is fitted to these points in a curve fitting stage 66. The center of mass may be obtained by a conventional algorithm sensitive to the edge outline of the respective teeth. In FIG. 8, where previously described stages have the same reference characters, the center of mass curve 62 is displayed in an overlay fashion in the stage 42 on the 3D model of the prosthesis. As described above in relation to FIG. 2, the misalignment between the overlay and the 3D model is determined in the alignment stage 44 and removed in the adjustment stage 46 by adjusting the size, shape, and position of the teeth involved in the prosthesis. Once the overlay of the curve and the 3D model match sufficiently, the prosthesis can be fabricated in the fabrication stage 48.

Figure 9:
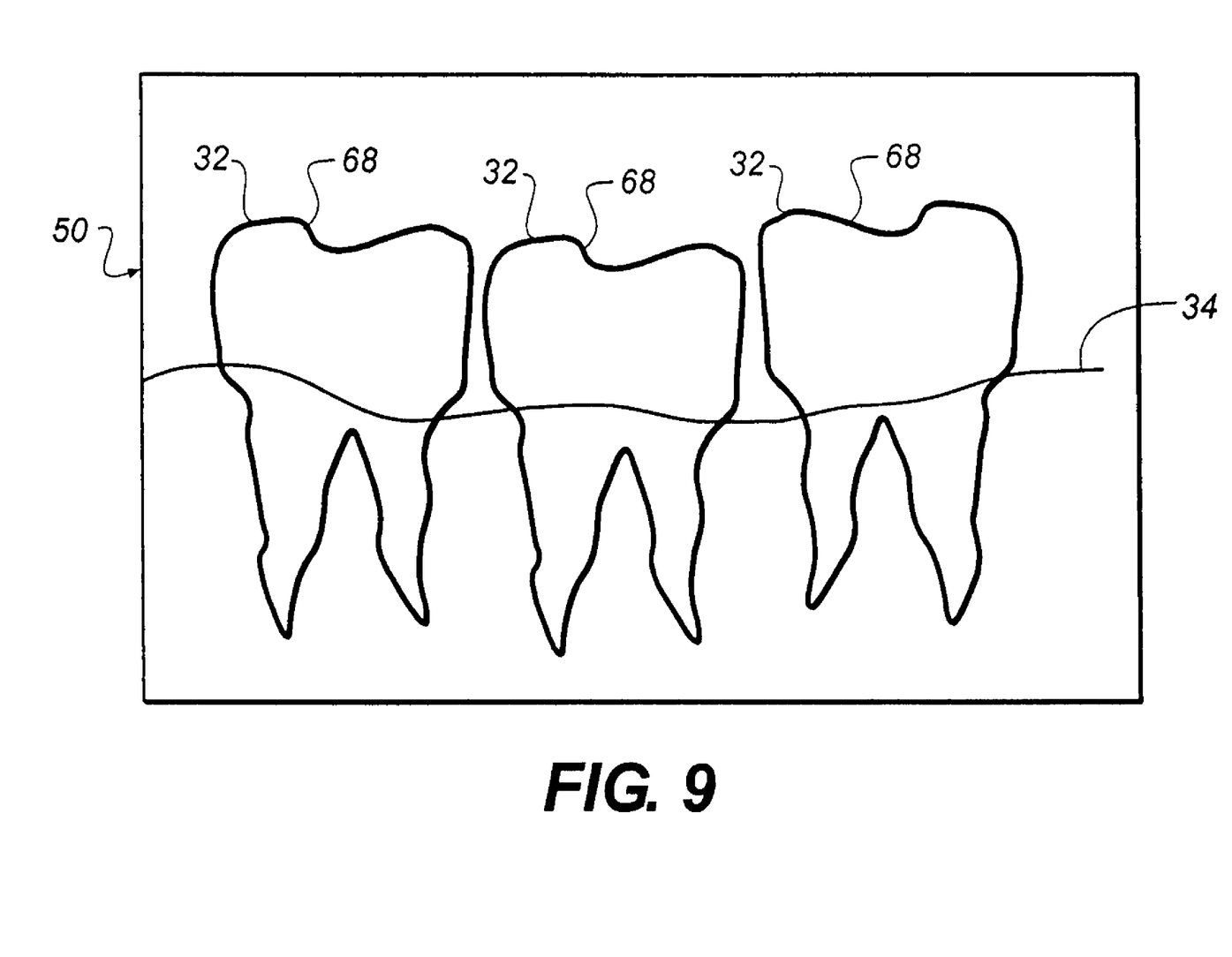
FIG. 9 shows an x-ray image illustrating an alternative method wherein the outline(s) of the teeth is computed.
Figure 10:
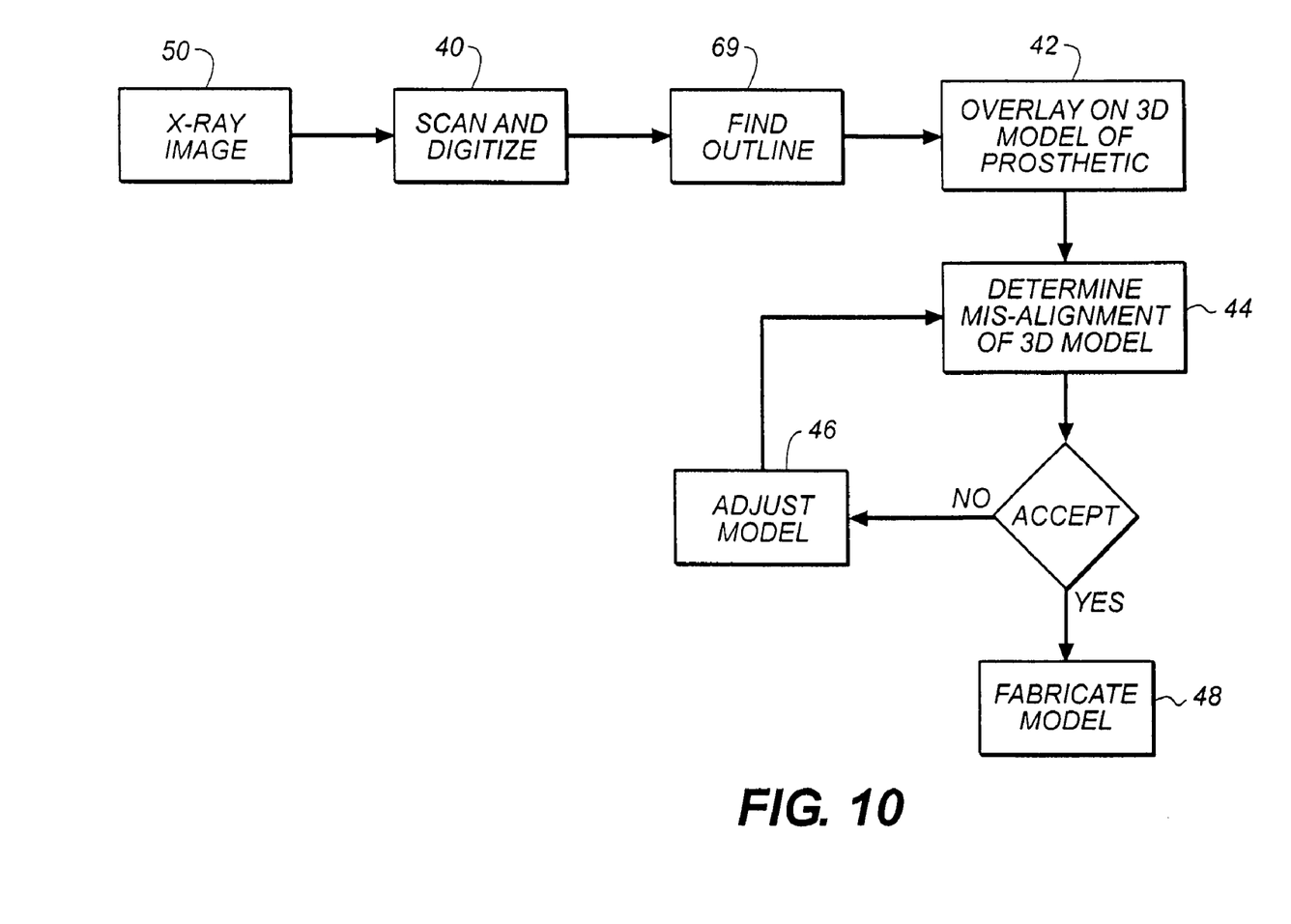
FIG. 10 shows a block diagram of a process for displaying the outline shown in FIG. 9 in an overlay fashion on the 3D model of the prosthesis.

FIG. 9 shows an example x-ray image 50 of an alternative method wherein the outline(s) 68 of the imaged teeth 32 is computed, and used as part of the comparison/adjustment process of FIG. 10, where an outline computing stage 69 is used to compute the outline 68. The outline computing stage 69 may use a conventional edge sensitive algorithm to identify the boundary pixels of each tooth. In FIG. 10, where previously described stages have the same reference characters, the outline 68 is displayed in an overlay fashion in the stage 42 on the 3D model of the prosthesis. As described above in relation to FIG. 2, the misalignment between the overlay and the 3D model is determined in the alignment stage 44 and removed in the adjustment stage 46 by adjusting the size, shape, and position of the teeth involved in the prosthesis. Once the overlay of the curve and the 3D model match sufficiently, the prosthesis can be fabricated in the fabrication stage 48.

Figure 11:
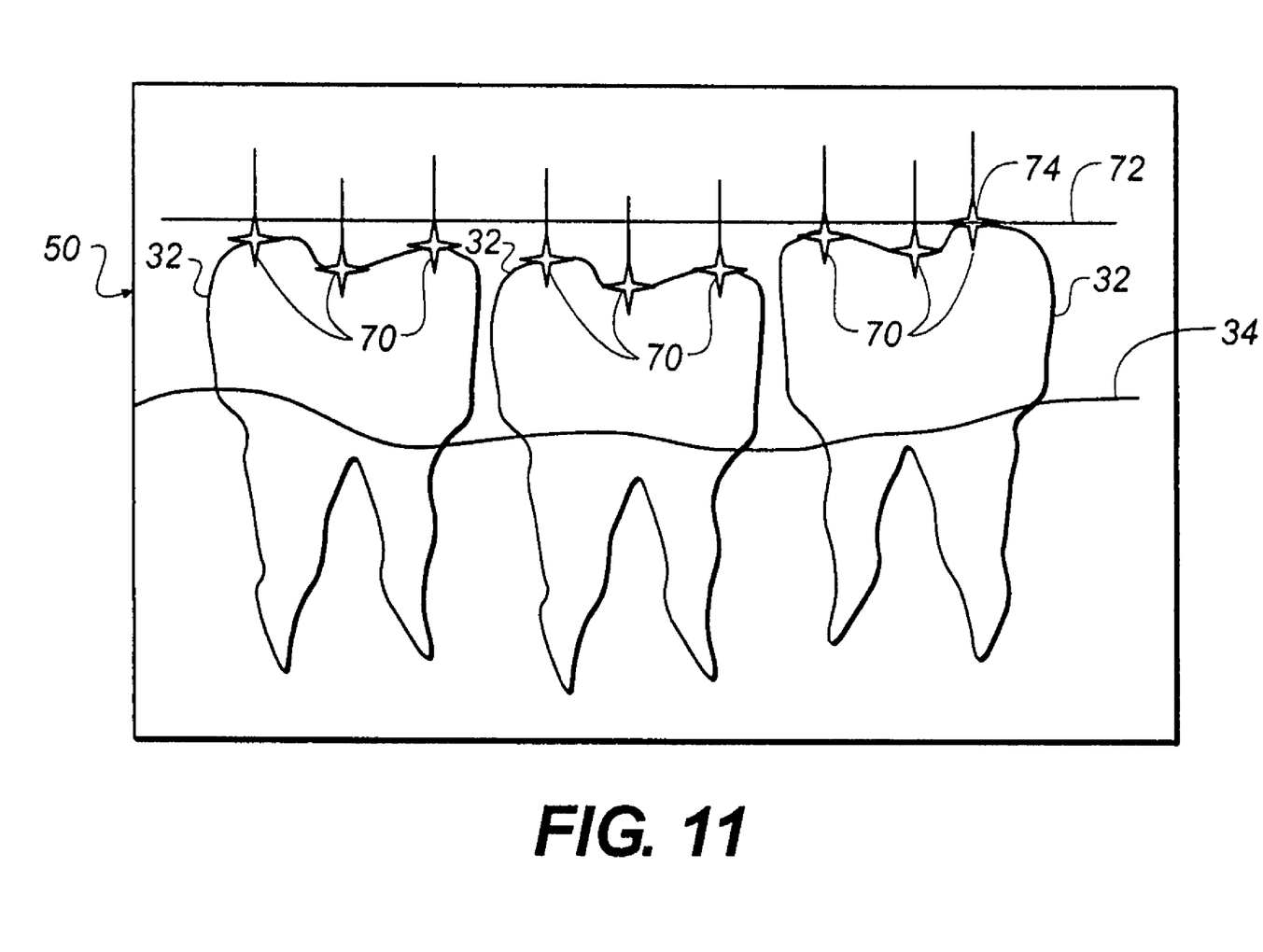
FIG. 11 shows an x-ray image illustrating an alternative embodiment that measures the displacement of key points on each tooth from a horizontally aligned vertical reference.
Figure 12:
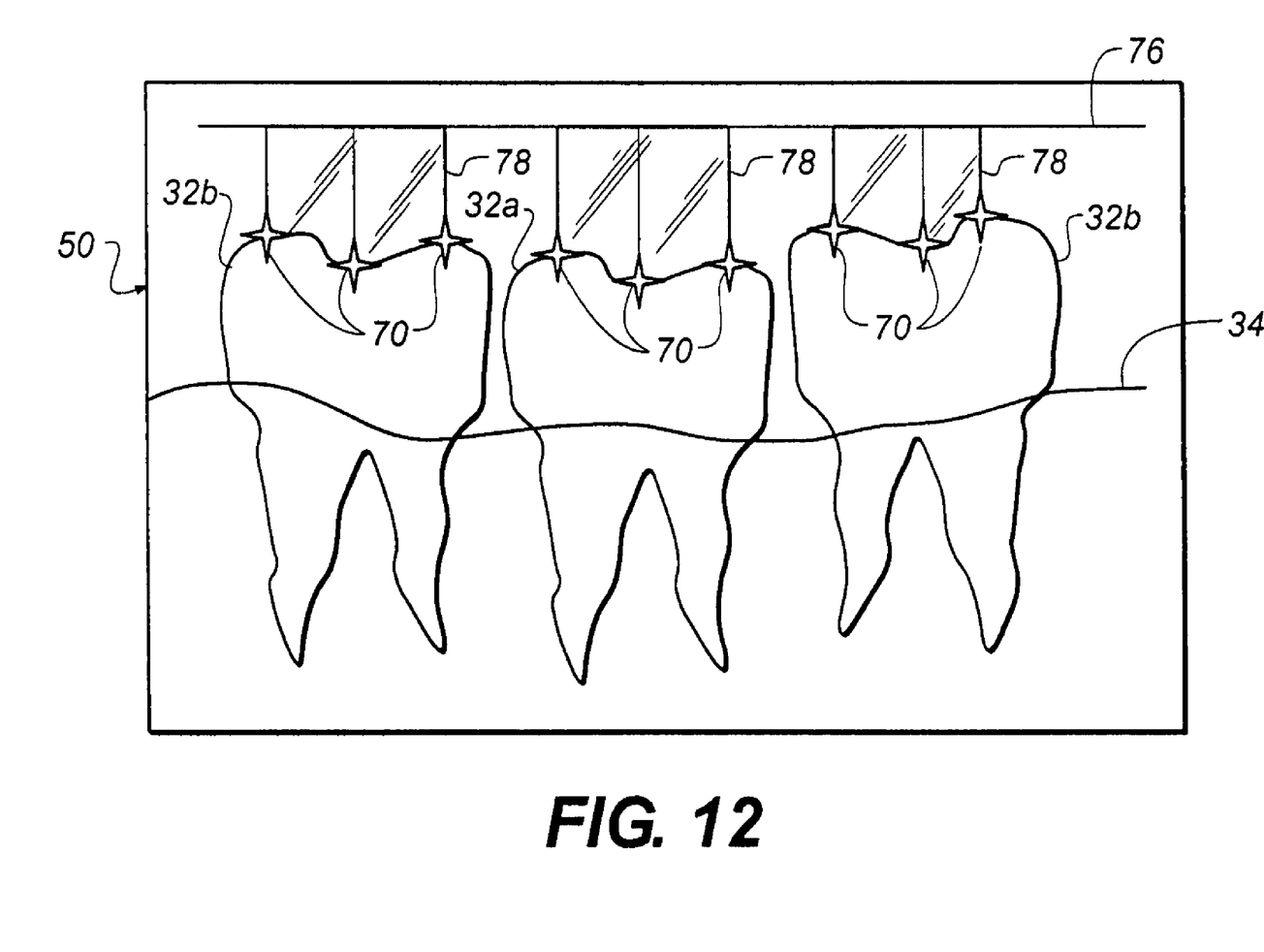
FIG. 12 shows an x-ray image illustrating an alternative that is independent of the gum line, measuring instead the relative distance from an arbitrary line.

FIG. 11 shows an example dental x-ray image 50 of an alternative embodiment in which the displacement of one or more key points 70 on each imaged tooth 32 is measured from a horizontally aligned vertical reference 72. In this case, the reference 72 is located relative to the highest point 74 on the teeth and to the position of the gum line 34. FIG. 12 shows an example dental x-ray image 50 of an alternative embodiment that is independent of the gum line 34, measuring instead the relative distance from an arbitrary line 76. This could be turned into a transparent template 78 or a fixture against which the relative fit of the prosthesis can be checked. In other words, the template 78 would be made so as to span the crown 32a (the repaired tooth) and the neighboring, existing teeth 32b. The dentist would place the crown 32a in position, prior to using adhesive, and use the template 78 to confirm the proper position of the crown 32a relative to the neighboring teeth 32b.

The invention has been described with reference to a preferred embodiment. However, it will be appreciated that variations and modifications can be effected by a person of ordinary skill in the art without departing from the scope of the invention.

PARTS LIST 1 capture stage
2 teeth
4 camera
6 computer system
8 3-dimensional model
10 machine tool
12 radiographs
14 scanner
16 processor
18 monitor
20 keyboard
22 mouse
24 cursor
26 milling cutter
28 restorative piece
30 dental x-ray
32 imaged teeth
32a crown
32b neighboring teeth
34 gum line
40 scanning stage
42 overlay stage
44 alignment stage
46 adjustment stage
48 fabrication stage
50 x-ray image
52 key vertices
54 fitted curve
56 vertices search stage
58 curve fitting stage
60 center of mass
62 curve
64 center of mass stage
66 curve fitting stage
68 outline
69 outline computing stage
70 key points
72 horizontally aligned vertical reference
74 highest point on the teeth
76 arbitrary line
78 transparent template

What is claimed is:

1. A method for determining dental alignment of a 3-dimensional model of one or more teeth of a patient for purpose of fitting a prosthesis, said method comprising the steps of:
   (a) obtaining a radiograph of the teeth of the patient;
   (b) obtaining a digital image from the radiograph indicative of the vertical alignment of the teeth relative to a gum line of the patient, wherein the alignment pertains to the relative vertical position of one or more of the patient's teeth as compared to adjacent teeth;
   (c) overlaying the 3-dimensional model of the teeth with the digital image obtained from the radiograph;
   (d) determining vertical and horizontal mis-alignment of at least three teeth in the 3-dimensional model relative to the digital image obtained from the radiograph; and
   (e) adjusting the 3-dimensional model to correct for nonlinear shape and mis-alignment, thereby producing an adjusted 3-dimensional model of the prosthesis that is corrected for the vertical and horizontal alignment of the teeth adjacent to the prosthesis and providing precisely fitted curvature data of the teeth as part of a dental arch.

2. The method as claimed in claim 1 wherein the adjusted 3-dimensional model is used to fabricate the prosthesis.

3. The method as claimed in claim 1 wherein the step (e) of adjusting the 3-dimensional model comprises adjusting size, shape and position of the prosthesis in the 3-dimensional model.

4. The method as claimed in claim 1 wherein the step (b) of obtaining the digital image comprises identifying key vertices of three or more teeth in the radiograph and fitting a vertices curve through the vertices.

5. The method as claimed in claim 4 wherein the step (c) of overlaying comprises overlaying the vertices curve over the 3-dimensional image whereby the curve is used in step (d) to determine mis-alignment.

6. The method as claimed in claim 1 wherein the step (b) of obtaining the digital image comprises identifying center of mass points of three or more teeth in the radiograph and fitting a center of mass curve through the center of mass points.

7. The method as claimed in claim 6 wherein the step (c) of overlaying comprises overlaying the center of mass curve over the 3-dimensional image such that the center of mass curve is used in step (d) to determine mis-alignment.

8. The method as claimed in claim 1 wherein the step (b) of obtaining the digital image comprises forming an outline of three or more teeth in the radiograph and wherein the outline is used in step (d) to determine mis-alignment.

9. The method as claimed in claim 2 further comprising the step of measuring the displacement of one or more key points on each tooth in the digital image from a horizontally aligned vertical reference, and using the displacement to form a template or fixture that can be used to check the fit of the prosthesis fabricated from the adjusted 3-dimensional model relative to the gum line.

10. The method as claimed in claim 9 wherein the horizontally aligned vertical reference is located relative to the highest point on the teeth and to the position of the gum line.

11. The method as claimed in claim 9 wherein the horizontally aligned vertical reference is an arbitrary distance from the teeth independent of the gum line.

* * * * *